United States Patent [19]
Nagji

[11] Patent Number: 5,505,908
[45] Date of Patent: Apr. 9, 1996

[54] RECYCLING AND RECOVERY OF METHYL BROMIDE FUMIGANT

[75] Inventor: Moez Nagji, Summerfield, N.C.

[73] Assignee: Halozone Technologies, Inc., Mississauga, Canada

[21] Appl. No.: 299,903

[22] Filed: Sep. 1, 1994

[51] Int. Cl.$^6$ ..................... A61L 9/00
[52] U.S. Cl. ............... 422/31; 95/131; 95/142; 422/30; 422/32; 422/122; 426/318
[58] Field of Search ............ 422/30, 31, 32, 422/120, 122, 306; 426/318, 419; 95/131, 142, 148, 123; 43/125

[56] References Cited

U.S. PATENT DOCUMENTS

| | | | |
|---|---|---|---|
| 3,041,684 | 7/1962 | Dawson et al. | 422/32 X |
| 3,206,275 | 9/1965 | Sair et al. | 422/33 |
| 3,608,273 | 9/1971 | Fabuss et al. | 95/148 |
| 4,018,704 | 4/1977 | Kuragano | 252/411 R |
| 4,256,773 | 3/1981 | Itoga et al. | 426/419 X |
| 4,322,394 | 3/1982 | Mezey et al. | 423/244 |
| 4,336,759 | 6/1982 | Winter | 95/148 X |
| 4,651,463 | 3/1987 | Friemel | 422/32 X |
| 4,748,013 | 5/1988 | Saito et al. | 95/131 X |
| 4,812,291 | 3/1989 | Friemel et al. | 422/30 X |
| 4,966,755 | 10/1990 | Smith | 422/30 X |
| 5,187,131 | 2/1993 | Tiggelbeck et al. | 502/34 |
| 5,259,853 | 11/1993 | Brasier et al. | 95/92 |
| 5,282,886 | 2/1994 | Kobayashi et al. | 95/131 |

OTHER PUBLICATIONS

Webster's Ninth New Collegiate Dictionary, Merriam–Webster Inc., 1990, p. 54.

Primary Examiner—Robert J. Warden
Assistant Examiner—Krisanne M. Thornton
Attorney, Agent, or Firm—Eugene Lieberstein; Michael N. Meller

[57] ABSTRACT

Unused methyl bromide from a fumigation cycle is captured by adsorption on a molecular sieve and recycled for reuse or recovery by desorption with hot gas without the need to purge the fumigation chamber with outside air. The loss of methyl bromide to the atmosphere is minimal.

7 Claims, 1 Drawing Sheet

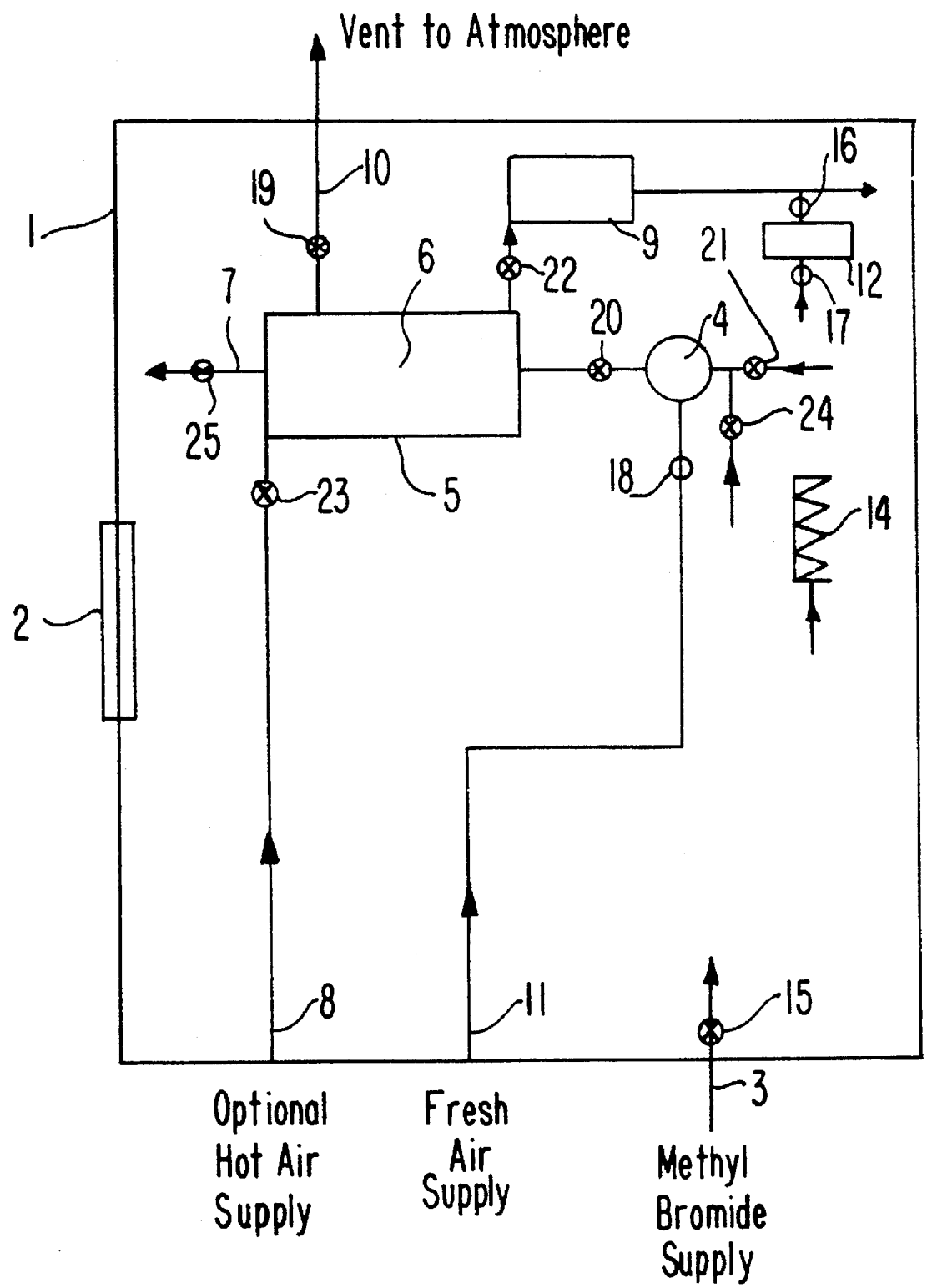

RECYCLING AND RECOVERY OF METHYL BROMIDE FUMIGANT

FIELD OF THE INVENTION

This invention relates to the field of fumigation of products with methyl bromide, and more particularly to a fumigation method in which methyl bromide is recycled and recovered for repeated use.

BACKGROUND OF THE INVENTION

Methyl bromide is widely used for fumigating fruits, vegetables, grains, soil, lumber and enclosures requiring a sterilized atmosphere. However, methyl bromide is now recognized as a major ozone depleting substance (ODP) and will be regulated with other ODP substances under the Montreal Protocol. While its ODP potential of 0.7 is high, a major concern is its ability to achieve that potential in a much shorter time span than chlorofluorocarbons (CFCs), making it more potentially damaging to the ozone layer in the next ten years.

The current method of fumigating fruits and vegetables or other produce with methyl bromide is to fill a chamber defining an enclosed space of, e.g. 1000 $ft^3$ to over 100,000 $ft^3$ with the produce. Pure methyl bromide is added to the chamber at a concentration of 10,000 to 20,000 ppm and maintained for several hours to ensure proper fumigation. For example, when fumigating cherries, 65 $g/m^3$ of methyl bromide is added to the chamber and maintained for 2 hours.

After the required time, the chamber is purged with huge amounts of fresh air and all the remaining methyl bromide is vented to the atmosphere. As only up to about 20% of the methyl bromide is actually consumed in the process, about 80% of the total methyl bromide must be vented to the atmosphere. In some cases, the methyl bromide is diluted with sufficient fresh air to attain a 500 ppm concentration in the effluent. In any event, no matter what the concentration, all of the unused methyl bromide must eventually be vented to the atmosphere.

Most fruit seasons are very short and it is economically valuable to shorten the cycle time to enable higher chamber utilization.

One purpose of the present invention is to prevent pollution of the atmosphere with methyl bromide during fumigation of a product.

Another purpose of the invention is to shorten the time between fumigation cycles.

A still further purpose of the invention is to recycle unused methyl bromide to the fumigation process.

SUMMARY OF THE INVENTION

The method according to the invention comprises the steps of:
(1) placing a product within an enclosure defining the space to be fumigated;
(2) sealing the enclosure,
(3) introducing a fumigatingly effective amount of methyl bromide into the enclosure to produce a gaseous atmosphere of air and methyl bromide,
(4) allowing the methyl bromide to remain in contact with the product for a predetermined length of time to ensure proper fumigation,
(5) circulating the gaseous atmosphere in the enclosure over at least one molecular sieve bed in an adsorption unit to adsorb methyl bromide until a selected enclosure concentration of methyl bromide is reached,
(6) blocking off the adsorption unit, and
(7) removing the fumigated product from the enclosure.
The method may additionally include the steps of:
(8) placing a new load of product into the enclosure,
(9) sealing the enclosure,
(10) introducing hot air into the adsorption unit to desorb all of the previously adsorbed methyl bromide forming an air/methyl bromide effluent,
(11) recirculating said effluent through the enclosure and the adsorption unit until an equilibrium is reached between the concentration of methyl bromide in the enclosure and the effluent from the adsorption unit, and
(12) adding sufficient methyl bromide into the enclosure to provide the fumigatingly effective amount required to start another fumigation cycle beginning with step (4).

If for any reason, it is not desirable to reuse the adsorbed methyl bromide in the fumigation chamber, the effluent may be cooled sufficiently to recover liquid methyl bromide to use for other purposes. For a single batch process, the method may terminate at step (7).

BRIEF DESCRIPTION OF DRAWING

The drawing is a flow diagram of the method according to the invention.

DETAILED DESCRIPTION

EXAMPLE OF PRIOR ART PROCESS

A 50,000 $ft^3$ chamber is filled with boxes of cherries. It is assumed that about 60% to 80% of the chamber is void volume so that 30,000 $ft^3$ to 40,000 $ft^3$ of air is present in the chamber. After the chamber is sealed, from about 175 to 233 lbs. (depending upon the temperature of the cherries) of 100% methyl bromide is introduced into the chamber to provide the required amount of methyl bromide to ensure proper fumigation. The methyl bromide is allowed to remain in contact with the cherries for about 2 hours. Then the chamber is purged. Four fans moving 5,000 to 10,000 SCFM are switched on. Air from the chamber can be vented directly to the atmosphere or it may be mixed with outside air and purged through a 25 ft stack. In the latter case, an analyzer controls the air flow from the chamber to ensure that the air outlet is closed if the concentration of methyl bromide in the effluent exceeds 500 ppm. The chamber is purged until the methyl bromide concentration in the chamber is about 5 ppm. At this point, the purging is stopped and the cherries are removed, ready to be exported.

EXAMPLE OF PROCESS ACCORDING TO THE INVENTION

The fumigation unit comprises a fumigation enclosed space defined by a chamber (1) having a sealable entry (2), a supply intake (3) for methyl bromide, a fan (4) for circulating the gaseous atmosphere in the chamber (1) through a molecular sieve adsorber unit (5) containing at least one molecular sieve bed (6) having an outlet (7) to the chamber, an optional hot air supply (8), a cooler (9), a vent (10) to the outside atmosphere, a heat exchanger (14) and a fresh air supply (11). Check valves 15, 16, 17 and 25 are used to open or close appropriate feed lines or pipes for carrying out the process of the present invention. An air analyzer unit (12) analyzes the methyl bromide content of the chamber atmosphere and the outlet air from the cooler (9) during regeneration.

In accordance with the flow diagram shown in the single drawing, after a fumigation step has been completed, instead of introducing fresh air into the chamber (1) to purge it, the gaseous atmosphere in the chamber is circulated by fan (4) over the molecular sieve bed (6) in the adsorption unit (5). The methyl bromide is adsorbed by the molecular sieve bed and the effluent is recycled back to the chamber through outlet (7). The air/methyl bromide effluent from the adsorption unit may be cooled to atmospheric temperature e.g. between 70°–105° F. before it is recirculated back to the chamber. It is generally accepted that an amount of air equivalent to 3 to 6 void volumes of the chamber are needed to purge the chamber. For example, for four (4) void volumes, 30,000 to 40,000 ft$^3$ of air would be needed. For a purging time of half an hour, 4000 to 5333 SCFM of air would have to be moved over the molecular sieve bed in order to remove the 210 lbs of methyl bromide remaining from the fumigation step. The moleculer sieve adsorption unit (5) can be designed to provide outlet specifications of well under 500 ppm, before the air is exhausted to the atmosphere through vent (10). The adsorption unit (5) is then blocked off, the fumigated cherries are removed and a new load of cherries to be fumigated is brought in. The entry (2) to the chamber is sealed and the regeneration of the adsorber unit is started.

Regeneration may occur in a closed cycle by drawing air from the chamber (1) through a heat exchanger (14) so that heated air will be introduced into the adsorption unit (5) from within the chamber (1) to desorb the methyl bromide and to simultaneously provide a sterilizing atmosphere for the new load of product. Alternatively, hot air may be supplied to the adsorption unit (5) from an optional hot air supply (8) which may be generated from within the chamber 1 or external of the chamber 1 Regeneration of unit (5) is preferably stopped when the air in the chamber (1) and the air effluent (7) exiting the molecular sieve bed are within 200 ppm, as determined by the air analyzer (12). The adsorption unit (5) may also be flushed with some fresh air from the fresh air supply (11) to purge any remaining methyl bromide in the voids of the molecular sieve bed and for cooling off the molecular sieve bed although, as explained hereafter, no cooling of the bed is necessary. The methyl bromide concentration in the chamber is adjusted to the required fumigation level by adding fresh methyl bromide from the methyl bromide supply (3). The steps following fumigation are then repeated as necessary. It should be apparent that the fumigation operation may be used for fumigating other fruits as well as cut flowers, grains, nuts, timber, etc., and may be applicable to any enclosure including a greenhouse, ship hold, etc.

Thus, a single bed adsorption unit provides a reservoir to capture the methyl bromide during the purging step in its gaseous state and as a source of methyl bromide for repeated fumigation. The methyl bromide is desorbed and recycled for reuse in one fumigation cycle, thereby not only protecting the environment but conserving methyl bromide. This adds to the economic advantage of a shortened fumigation cycle.

Although the adsorption unit is shown in the drawing as located within the fumigation chamber, it is of course possible and in some instances desirable to locate the unit outside of the chamber.

The preferred molecular sieve used in the process according to the invention includes the commercially available S-115 Silicalite, sold by Union Carbide Corporation and ZSM5 zeolite. The silicalite is not strictly speaking a zeolite because it has no ion-exchange capacity. It is a hydrophobic material containing more than 99% $SiO_2$, having a pore volume of 0.19 cc/gm and a pore size approximately 0.6 angstroms in diameter. The ZSM5, on the other hand, is an organophilic, hydrophobic Y-type zeolite as disclosed in U.S. Pat. No. 3,702,888. This zeolite has a pore size of about 6 angstroms and a Si:Al ratio of 15 up to 1000. Volatile hydrocarbons emitted by fruit are not adsorbed by the silicalite or the zeolite in the presence of methyl bromide.

In a conventional adsorption system, the adsorption unit needs to be cooled after heating. In the system according to the invention, no cooling of the bed is necessary since the methyl bromide is recirculated into the chamber. During the next adsorption step, the bed gets cooled and starts readsorbing. In a conventional system, this cannot be done as during the adsorption/cooling step, the contaminant would slip through. If it is a closed loop, the desorbed methyl bromide will be recirculated while heating the molecular sieve bed. At the end of the heating step, the ppm level of methyl bromide in the chamber is close to the ppm level at the start of the adsorption. Tests have shown that the residual MeBr in the piping and adsorption unit (5) is between 10% and about 30% of the total MeBr in the chamber at the beginning of the adsorption cycle whereas, if an open cooling step, as is conventional, is applied, the residual MeBr would be lost to the atmosphere. Thus, during the first adsorption cycle 10 to 30% of the MeBr is not returned to the Chamber. However, subsequent cycle experiments have shown that close to 100% of the MeBr in the chamber at the start of adsorption is indeed returned to the chamber. As the regeneration is done with MeBr containing regenerated gas, the adsorbent of choice has to have the least residual loadings at the heating temperature to provide maximum working loadings.

It is understood that other variations of the process may be made without departing from the scope of the invention as defined in the claims.

I claim:

1. A method for fumigating a product comprising the steps of:

(1) providing an enclosure defining a confined space to be fumigated, (2) placing a product within the enclosure, (3) sealing the enclosure, (4) introducing a fumigatingly effective amount of methyl bromide into the enclosure to produce a gaseous atmosphere of air and methyl bromide, (5) allowing the methyl bromide to remain in contact with the product for a predetermined length of time to ensure proper fumigation, (6) circulating the gaseous atmosphere in the enclosure over at least one molecular sieve bed in an adsorption unit to adsorb methyl bromide until a selected concentration of methyl bromide is reached, (7) blocking off the adsorption unit from the gaseous atmosphere in the enclosure, (8) removing the fumigated product from the enclosure, (9) placing another load of product into the enclosure,

(10) sealing the enclosure,

(11) introducing air into the adsorption unit at a temperature high enough to desorb all of the previously adsorbed methyl bromide and to form an air/methyl bromide effluent,

(12) recirculating the effluent through the chamber and the adsorption unit until an equilibrium is reached between the concentration of methyl bromide in the enclosure and the effluent from the adsorption unit, and

(13) adding sufficient methyl bromide to provide the fumigatingly effective amount required to start another fumigation cycle according to step (4).

2. The method according to claim 1, wherein the air passed through the molecular sieve bed is heated to the desired temperature to form an air/methyl bromide effluent and is supplied from a hot air supply.

3. The method according to claim 1, wherein the molecular sieve is an organophilic, hydrophobic Y-type molecular sieve having a pore size of about 6 angstroms in diameter and a Si:Al ratio of 15–1000.

4. The method according to claim 1, wherein the molecular sieve is a silicalite containing more than 99% $SiO_2$ and having a pore size of approximately 0.6 angstroms in diameter.

5. The method according to claim 1, wherein the effluent from step (6) is cooled to about 70–105° F.

6. The method according to claim 1, wherein air from the enclosure is heated to provide the air for step (11).

7. The method according to claim 1, wherein fresh air is heated to provide the air for step (11).

* * * * *